United States Patent [19]

Berkey et al.

[11] 4,117,396
[45] Sep. 26, 1978

[54] SENSOR FOR THERMALLY IONIZABLE PARTICLES AND/OR VAPORS

[75] Inventors: Edgar Berkey, Murrysville; William H. Reed, III, Monroeville; William M. Hickam, Pittsburgh, all of Pa.

[73] Assignee: Westinghouse Electric Corp., Pittsburgh, Pa.

[21] Appl. No.: 435,389

[22] Filed: Jan. 21, 1974

[51] Int. Cl.² .................. G01N 27/00; E21B 11/02
[52] U.S. Cl. ................................. 324/33; 126/19 R
[58] Field of Search .............. 324/33; 176/19; 165/11; 73/40.7, 19, 23; 250/251

[56] References Cited

U.S. PATENT DOCUMENTS

| | | | |
|---|---|---|---|
| 2,790,949 | 4/1957 | Ottinger et al. | 324/33 |
| 3,154,680 | 10/1964 | Greene | 324/33 X |
| 3,166,901 | 1/1965 | Bliss | 176/19 LD X |
| 3,439,262 | 4/1969 | Roberts | 324/33 |
| 3,465,727 | 9/1969 | Tidball | 165/8 C |
| 3,808,433 | 4/1974 | Fite et al. | 250/251 |

FOREIGN PATENT DOCUMENTS 2,452,044 5/1975 Fed. Rep. of Germany041161365.

*Primary Examiner*—R. V. Rolinec
*Assistant Examiner*—Rolf Hille
*Attorney, Agent, or Firm*—M. P. Lynch

[57] ABSTRACT

A sensor for detecting the presence of thermally ionizable particles and vapors is disclosed. The sensor comprises an ionizer for supplying sufficient heat to thermally ionize the particles to be detected. The ionized particles are then caused to flow between the ionizer and an anode by impressing an electrical potential between the ionizer and the anode. The magnitude of the ion current is indicative of the concentration of the particles of vapors to be detected. The sensor is particularly useful in detecting alkali vapors and other particles, for example sodium, which may be easily thermally ionized. In most applications it is contemplated that the sensor will serve as a detector for alkali vapors and particles present in a gaseous atmosphere. Specifically it will serve as a detector for locating leaks in components of the fast breeder nuclear reactor system which employs sodium as a heat exchanger fluid.

2 Claims, 6 Drawing Figures

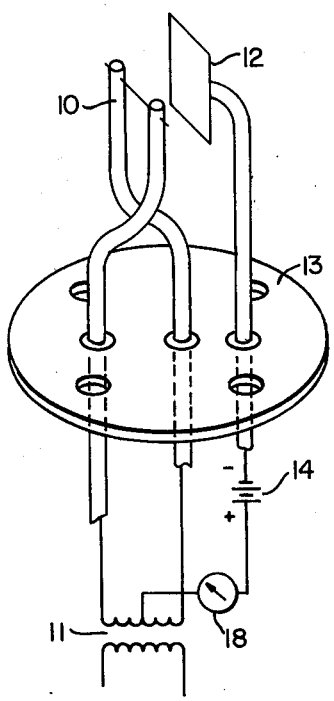
FIG.1
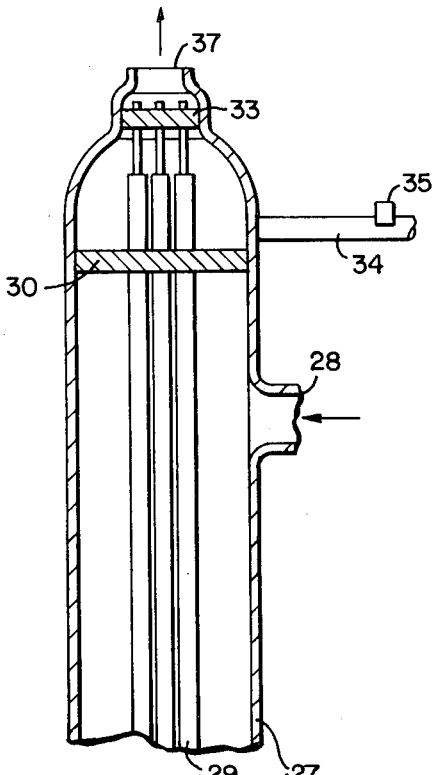
FIG.4
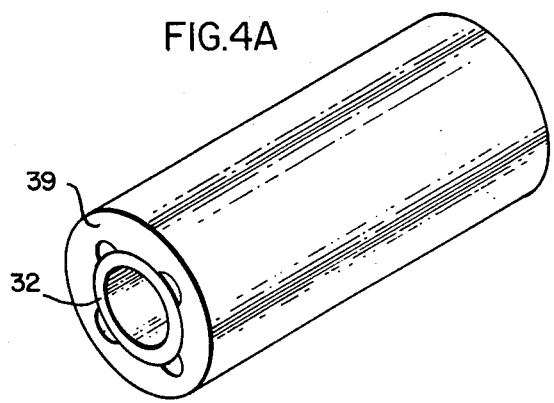
FIG.4A
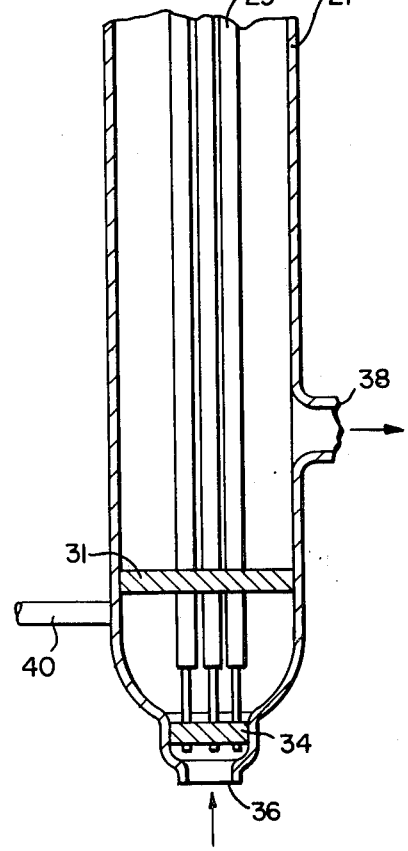

SENSOR FOR THERMALLY IONIZABLE PARTICLES AND/OR VAPORS

BACKGROUND OF THE INVENTION

FIELD OF THE INVENTION

The invention relates to sensors and more specifically to sensors for detecting thermally ionizable particles, vapors or mixtures of such particles or vapors.

SUMMARY OF THE INVENTION

The sensor which is the subject of this invention includes an ionizing member which operates at a temperature sufficiently high to thermally ionize the particles or vapors to be detected. An anode is positioned such that it is near but not in contact with the ionizing member. An electrical voltage is connected between the ionizing member and the anode such that the anode is negative with respect to the ionizing member.

When the atoms or molecules also referred to as particles containing elements which are easily thermally ionized such as sodium, potassium or lithium come near the ionizing member, positive ions are formed from these elements. The ions are attracted to the anode causing a current to flow between the ionizer and the anode. Since substantially all of the current flowing between the ionizer and the anode are caused by these ions, the magnitude of the current can be related to the concentration of elements from which these ions are formed.

The sensor can be utilized to detect the easily ionizable elements or molecules in air or atmospheres containing a significant amount of water vapor and oxygen because the molecules of the water vapor and oxygen are not easily thermally ionized. It is contemplated that the vapor detector will find a significant application in the detection of sodium leaks in liquid metal fast breeder nuclear reactors and equipment associated therewith.

Since the pressure to which the filament and the anode are subjected is not a parameter critical to the performance of the sensor, it is capable of detecting thermally ionized particles and vapors under both high pressure and reduced pressure conditions. Therefore, it also has utility as an alkali leak detector for vacuum systems.

DESCRIPTION OF THE DRAWINGS

FIG. 1 is a drawing of the sensor;

FIG. 4 illustrates how the sensor may be used for detecting sodium leaks in a steam generator utilizing the duplex tubes; and FIG. 4a is a cross section view of one of the tubes used in the heat exchanger illustrated in FIG. 4.

DETAILED DESCRIPTION

Figure 3:
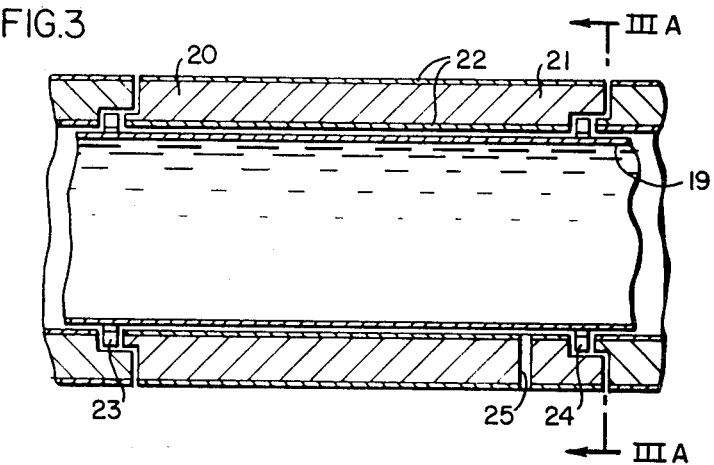
FIG. 3 illustrates how the sensor may be used for detecting leaks in a pipe carrying high temperature sodium.

The basic structural details of the sensor are illustrated in FIG. 1. The sensor includes a filament 10 which functions as an ionizer when heated. The filament is heated to a temperature in the neighborhood of 1000° C. by passing current through the filament. The current is provided by a transformer 11. It is convenient to provide power to the filament from a 110 volt A.C. line and step the voltage down to approximately one volt by transformer 11. The current through the filament 10 causes the temperature of the filament to increase to approximately 1000° C. Temperatures above 800° C. are sufficient to cause atoms or molecules containing elements such as sodium, potassium or lithium which come near or in contact with the filament to be ionized.

An anode 12 is positioned near but not in electrical contact with the filament 10. The leads from the filament 10 and the anode 12 pass through a supporting base 13. The base may be any suitable material if the leads to the anode 12 and the filament 10 are sufficiently insulated from the base. In applications where the detector will operate in a relatively high pressure or where all metallic construction is required the base 13 may be steel with insulators to electrically insulate the anode and filament leads. A flange type base is illustrated in FIG. 1 as a matter of convenience.

A voltage source 14 is connected between the anode lead and the filament. This is conveniently done by providing a center tap to the transformer 11 which supplies current to the filaments. Included in the lead between the voltage supply 14 and the center tap of the filament transformer 11 is a current meter 18.

As previously described, atoms or molecules containing easily thermally ionized elements of the type detected by the sensor, which come in contact with or near to the hot filament 10 are ionized. When the ions are formed they will be attracted to the anode 12 causing a current to flow in the filament anode circuit. Using simplifying assumptions this current can be predicted theoretically from the following equation:

$$I \text{ (amps)} = \frac{(1.6 \times 10^{-19})(\pi DL)\nu P_{Na}}{(1 + \frac{1}{\exp(11606[\omega - IP]/T)})} \quad (1)$$

where:

I = measured plate current, amps
D = filament diameter, cm
L = filament length, cm
$P_{Na}$ = partial pressure of Na, atm
$\omega$ = work function of the filament, V
IP = ionization potential of Na, V
T = temperature of filament, ° K.
$\nu = (3.513 \times 10^{22}) P (MT^*)^{-\frac{1}{2}}$, number of molecules/cm²sec where:

P = gas pressure, mm
M = molecular weight of carrier gas
T* = temperature of carrier gas, ° K.

The equation describes theoretically the functioning of the sensor. Data obtained using the sensor correlates favorably with theoretical predictions.

Figure 2:
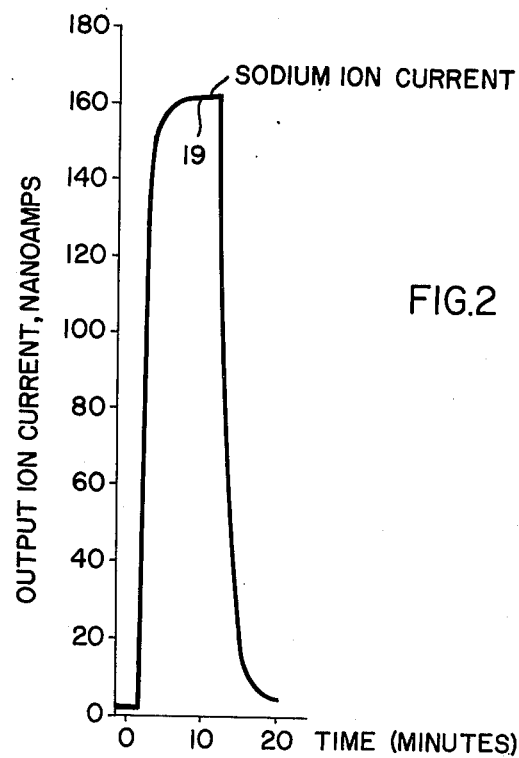
FIG. 2 is a diagram illustrating the change in ion current through the sensor as sodium is introduced into the atmosphere surrounding the sensor.

FIG. 2 is an experimental curve showing the ion current as a function of time on introduction of sodium into the argon flowing through the sensor. The fast time response enables rapid detection of leakage conditions. The decay of the ion current shows the fast recovery of the sensor to sodium depletion. Similar curves have been obtained when sodium is introduced into flowing nitrogen containing additions of water vapor and oxygen.

In the experimental sensor the filament was made of Thoriated Iridium. The anode was made of Molybdenum. Nickel or stainless steel may also be used to construct the anode. Other materials may also be used to construct the filament.

Filament life is principally determined by the filament material, the operating temperature and the environment to which the filament is subjected. Although a single filament is shown, the sensor could employ a multiple filament system where each filament can be independently energized. This negates the need for sensor replacement in the event of filament failure. Sensor design incorporating replaceable filament assemblies could further reduce sensor maintenance and cost of operation.

FIG. 3 illustrates how the detector may be utilized to detect sodium leaks in piping of the type which is anticipated to be used in liquid metal cooled fast breeder reactors and other parts of the system such as the heat exchanger. In this application, it is anticipated that the sodium carrying pipe will be encased in rigid insulating members which are held in spaced relationship to the pipe. A typical pipe and insulating member are illustrated in cross section in FIG. 3. The pipe 19 would normally be of high quality stainless steel. The pipe would be encased by segments of insulation with a typical segment being illustrated in cross section at reference numeral 20. The insulating member normally includes a middle layer of material having a low heat transfer coefficient sandwiched between two concentric stainless steel cylinders. The insulating material and the concentric stainless steel cylinders are respectively illustrated at reference numerals 21 and 22. The insulating sections are held positioned away from the stainless steel sodium flow pipe 19 by spacers illustrated at reference numerals 23 and 24. A primarily nitrogen or other inert gaseous atmosphere will normally be provided between the pipe carrying the sodium 19 and the inner surface of the insulating member 20. An opening 25 for the detector is provided in the insulating member. This permits the filament and anode of the sensor to be positioned such that they are in contact with the atmosphere existing between the insulating member 20 and the sodium carrying pipe 19. Any leakage in the sodium carrying pipe 19 will cause sodium to leak into the space between the pipe 19 and the insulating member. This sodium will be detected by the sensor positioned in the opening to produce a signal indicating the presence of the sodium. The sensitivity of the detector is sufficient to detect the early presence of the sodium before it builds up to a concentration sufficient to cause serious damage such as excessive corrosion or fires. The sensor is not shown in detail in order to simplify the drawing.

Figure 3A:
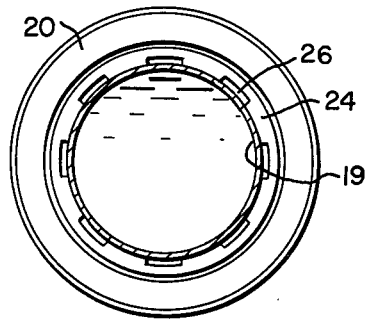
FIG. 3a is a cross section view of the pipe illustrated in FIG. 3.

The end view of the pipe, the insulating member and the spacers are illustrated in more detail in FIG. 3A. In this figure it can clearly be seen that the spacer 24 includes a plurality of longitudinal openings 26 which permits the nitrogen to flow along the space between the insulating member 20 and the sodium carrying pipe 19. This enables the space to be continually or periodically purged with an inert gas such as nitrogen. The presence of the flowing gas permits fewer detectors to be used because sodium from a leak a considerable distance away will be transported to the detector by the flowing inert gas without substantial delay. Other detail configurations of the insulating member 20, the sodium pipe, and the detector insulations could also be used so long as the configuration assures that sodium leaks anywhere in the pipe 19 would be detected in a relatively short time. It is also recognized that the sensor has utility as a sodium sniffer. In this mode of operation the sensor could be utilized to scan the system for sodium leaks and their location. For example, the atmosphere near the surface of the system would be sampled by a probe and drawn to the sensor to detect the presence of sodium. Both the sensor and the sample probe could be portable for use in detecting and locating sodium leaks over a wide area. The sensor could be permanently mounted, while the probe is connected to the sensor by a flexible hose for transporting the sample of the atmosphere to the sensor.

FIG. 4 illustrates how the detector can be utilized to detect sodium leaks in a steam generator which uses duplex heat exchanger tubes and sodium as the heat exchange fluid. A typical heat exchanger includes an outer wall 27. Typically this outer wall 27 would be of stainless steel or some other similar material since it is in direct contact with the sodium. The hot liquid sodium from the reactor flow into the inlet 28, around the duplex tube heat exchange tubes 29, and leaves the heat exchanger via an outlet 38 near the other end of the heat exchanger. Near each end of the heat exchanger are two sodium sealing plates 30 and 31. These plates are typically welded to the outer wall 27 of the heat exchangers and to the outer walls of the heat exchanger tubes 29. This completely seals the heat exchanger to assure that any sodium entering the sodium inlet 28 must emerge at the sodium outlet 38.

A cross section of a typical duplex heat exchanger tube is illustrated in FIG. 4A. The dual wall tube comprises two concentrically mounted tubes with the inner wall of the outer tube having longitudinal grooves therein. The outer tube is illustrated at reference numeral 39 and the inner tube is illustrated at reference numeral 32. In this tube the steam or water, depending on which end of the heat exchanger is being considered flows in the inner tubes. Helium is present in the grooves and the space between the inner wall of the outer tube and the outer wall of the inner tube while the outer wall of each of the tubes is in direct contact with the hot sodium. This type of tube is particularly advantageous in that both the inner and outer tubes must fail before there can be any contact between the steam or water in the inner tube and the sodium. Additionally, the helium filled space between the inner and outer tubes can be continuously monitored for the presence of sodium. This permits sodium leaks in the outer tube to be detected, as evidence of the loss of the dual protection provided by the duplex tube.

As previously discussed the plates 30 and 31 are welded to the outer tube 39. The ends of each of the heat exchanger tubes 29 are structured such that the inner tube 32 is substantially longer than the outer tube 39. Near the ends of the outer wall 27 of a heat exchanger two second sealing plates 33 and 34 are placed such that the plates are welded to the outer wall of the inner tube 32 and to the inner wall of the heat exchanger. The space between the inner and outer tube communicates with the plenum spaces between plates 31 and 34 and plates 30 and 33. Access to this space is provided by pipes 40 and 34. This total space is helium filled. The sodium sensor 35 positioned in pipe 34 will detect sodium entering this total space. A continuous or periodic flow of helium through this total space toward the sensor 35 will assist in the transport of sodium vapors to the sensor and provides a faster sensor response to a sodium leak.

Near the bottom end of the heat exchanger a water inlet 36 is provided. This water flows through the inner tube 32 of each of the heat exchanger tubes 29 through the entire length of the heat exchanger and emerges at the top end via a steam outlet 37. The sealing plates 33 and 34 isolate the water and the steam from the helium. In this manner, the combination of the steam generator and detector illustrated in FIG. 4 provides a reliable means for extracting heat from the liquid sodium to generate steam. It also permits early detection of sodium leaks so that corrective action can be taken prior to the occurrence of serious damage.

From the prior discussion it is obvious that an accurate and reliable sensor for thermally ionizable particles and vapors has been disclosed. The use of this sensor in conjunction with systems utilizing liquid sodium have been illustrated in detail. It is obvious that this sensor could also be employed in similar systems and processes utilizing other elements or compounds of these elements so long as the elements or the compounds of the elements are easily ionized thermally. It is recognized also that the sensor has utility for control purposes of these same systems and processes. The electrical output signal is of a convenient form for serving this function. Although a thoriated-iridium filament has been described it is recognized that other filament materials may be more resistant to attack by chemically reactive impurities. Other modifications of the system can also be made.

We claim:

1. A sodium vapor detector, comprising, a heated thermal ionizer means adapted to respond to impinging sodium vapor present in a carrier gas by ionizing sodium atoms to produce positive ions, said thermal ionizer means comprising a heated element having composition characteristics to produce an ion current in accordance with the following equation:

$$I \text{ (amps)} = \frac{(1.6 \times 10^{-19})(\pi D L v P_{Na})}{(1 + \frac{1}{\exp(11606[\omega - IP]/T)})}$$

where:
- I = measured current, amps
- D = element diameter, cm
- L = element length, cm
- $P_{Na}$ = partial pressure of sodium, atm
- $\omega$ = work function of the element, V
- IP = ionization potential of sodium, V
- T = temperature of element, °K.
- $v = (3.513 \times 10^{22}) P (MT^*)^{-\frac{1}{2}}$, number of molecules/cm²sec where:
- P = gas pressure, mm
- M = molecular weight of carrier gas
- T* = temperature of carrier gas, °K.—, and anode means spaced apart from said thermal ionizer means, means for applying an electrical potential between said thermal ionizer means and said anode means to attract said positive ions and establish said ion current flow between said thermal ionizer means and said anode means, the magnitude of said ion current being indicative of the concentration of sodium vapor present at said thermal ionizer means, and means operatively connected to said thermal ionizer means and said anode means to monitor said ion current.

2. A sodium vapor detector as claimed in claim 1 further including means for heating said thermal ionizer means to a temperature between 800° C. and 1000° C.

* * * * *